(12) United States Patent
Fujishima et al.

(10) Patent No.: US 6,352,850 B1
(45) Date of Patent: Mar. 5, 2002

(54) CHITINASE AND METHOD FOR PREPARING THE SAME

(75) Inventors: Shizu Fujishima; Naoko Yamano, both of Ikeda; Akihiko Maruyama; Takanori Higashihara, both of Tsukuba, all of (JP)

(73) Assignee: Agency of Industrial Science & Technology, Tokyo (JP)

( * ) Notice: Subject to any disclaimer, the term of this patent is extended or adjusted under 35 U.S.C. 154(b) by 0 days.

(21) Appl. No.: 09/661,808

(22) Filed: Sep. 14, 2000

(30) Foreign Application Priority Data

Oct. 27, 1999 (JP) ............................................ 11-304814

(51) Int. Cl.$^7$ ................................................. C12N 9/24
(52) U.S. Cl. ........................................................ 435/200
(58) Field of Search ........................................... 435/200

(56) References Cited

U.S. PATENT DOCUMENTS

| | | | | |
|---|---|---|---|---|
| 5,587,292 A | * | 12/1996 | Laine et al. | 435/201 |
| 5,744,325 A | * | 4/1998 | Fujishima et al. | 435/227 |
| 6,121,420 A | * | 9/2000 | Laine | 530/350 |

OTHER PUBLICATIONS

Computer Derwent Abstract 1994–172744 Mercian Corp JP 06113846 Pub Apr. 1994.*

Computer Caplus Abstract 2000:559302 Suginta et al "Chitinases from Vibrio. . . " J.Appl.Microbiol (2000) 89(1) 76–84.*

Computer Caplus Abstract 2000:363759 Babenko et al. "The isolation of endochitinase from Vibrio SP X and Some characteristics of the Enzyme" Biotek. (2000) (1) 39–45.*

Computer Caplus Abstract 1996:8198 Osawa et al "An investigation of Aquatic Bacteria Capable of Utilizing Chitin as the Sole Source of Nutrients" Lett Appl. Microbiol. (1995) 21 (5) 288–91.*

* cited by examiner

*Primary Examiner*—Herbert J. Lilling
(74) *Attorney, Agent, or Firm*—Rader, Fishman & Grauer, PLLC

(57) ABSTRACT

Chitinase with the following physico-chemical properties 1 to 6:

1. action: random cutting of the β-1,4 bond of chitin to generate the tetramer and dimer of Nacetylglucosamine;
2. optimum pH: 6.5 to 10.4;
3. stable pH: 7.0 to 9.0;
4. optimum temperature: 37° C.;
5. active temperature range: 4 to 60° C.; and
6. thermal stability: 60% or more of the initial activity as retained even after heating at 40° C. and pH 8.0 for 30 minutes; and a method for producing chitinase, comprising culturing a chitinase-generating bacterium reacting with chitin to generate the N-acetylglucosamine oligomer and collecting chitinase from the culture.

2 Claims, 2 Drawing Sheets

CHITINASE AND METHOD FOR PREPARING THE SAME

BACKGROUND OF THE INVENTION

1. Field of the Invention

The present invention relates to novel chitinase and a method for preparing the same.

2. Description of the Related Art

Chitin is an insoluble polysaccharide consisting of β-(1, 4)-linked N-acetylglucosamine and is present widely in the bacterial kingdom, plant kingdom and animal kingdom. Chitin is at a yearly production comparative to that of cellulose and is considered as one of the most abundant biomass resources.

Compounds in various chain lengths as recovered by hydrolysis of chitin have increasingly been used, together with chitosan as a deacetylated product of chitin, in a wide variety of fields including medicine, food, cosmetics, agriculture and garments. Particularly, chitin-derived low-molecular N-acetylglucosamine oligomer is known to have useful physiological activities such as immunopotentiation, anti-bacterial activity and anti-vial activity.

Conventionally, the N-acetylglucosamine oligomer has been commonly produced by thermally treating the shell of crab and shrimp in sodium hydroxide solution thereby removing protein, and removing ash with hydrochloric acid to recover chitin, and then preparing the resulting chitin into low-molecular substances by the limited hydrochloride hydrolysis method. Additionally, a method using hydrogen fluoride has been proposed recently.

However, any of these methods is disadvantageous in that the disposal of the equipment and liquid waste requires high cost. Furthermore, the essential bonds are readily cut so that the resulting production efficiency is unavoidably low due to the resulting byproducts.

Because chitinase as chitin decomposition enzyme acts only on certain predetermined sites in chitin under mild reaction conditions owing to the substrate specificity so that less byproducts are generated, cost reduction is possible. Therefore, industrially applicable methods for producing chitinase have been demanded. Currently, chitinase species derived from microorganisms of genera *Bacillus, Serratia*, and streptomyces are-commercially available for the purpose of using the chitinase species for academic research works but are so expensive. Additionally, these chitinase species are at optimum pH in acidity (pH 2 to 6). Thus, these chitinase species are not suitable for use at a range of pHs above neutrality. Additionally, the temperature range in which these chitinase species exert their action is narrow (the active temperature range of 30° C. to 45° C.).

The optimum pH in an acidic region requires corrosion-resistant equipment, disadvantageously, leading to the burden of cost. The narrow active temperature range requires laborious works for temperature control.

It is also reported that microorganisms of the genus Vibrio generate chitinase, but the microorganisms are all mesophilic microorganisms derived from the genus Vibrio [Akio Ohtakara, Masaru Mitsutomi and Yasushi Uchida, J. Ferment. Technol., 57, 169–177 (1979)]. It has never been known that psychrotrophic microorganisms of the genus Vibrio generate chitinase. Mesophilic microorganisms of the genus Vibrio at the optimum temperature at 30° C. to 40° C. require strict temperature control; and additionally, the thermal stability thereof reaches the threshold at 30° C. to 35° C. Thus, the mesophilic microorganisms of the genus Vibrio are likely to be inactivated, disadvantageously.

SUMMARY OF THE INVENTION

It is a purpose of the invention to provide a novel chitinase with the optimum pH principally around neutrality and in alkalinity, a wide active temperature range and useful functions and a method for producing the same.

Based on the fact that a vast amount of chitin is generated in ocean and is then decomposed with microorganisms, which serves for the ecological system in ocean, the present inventors have made investigations about chitinase production with marine bacteria. Consequently, the inventors have found that a marine psychrotrophic bacterial strain of the genus Vibrio generates a novel chitinase species with functions advantageous for industrial use, at high efficiency. Based on the finding, the invention has been achieved.

More specifically, the invention relates to chitinase with the following physico-chemical properties.

1. Action: Random cleavage of chitin β-1,4 bond to generate the tetramer and dimer of N-acetylglucosamine.
2. Optimum pH: 6.5 to 10.4.
3. Stable pH: 7.0 to 9.0.
4. Optimum temperature: 37° C.
5. Active temperature range: 4 to 60° C.
6. Thermal stability: 60% or more of the initial activity is retained even after heating at 40° C. and pH 8.0 for 30 minutes.

The invention; furthermore relates to a method for producing the chitinase, comprising culturing a chitinase-generating bacterium reacting with chitin to generate N-acetylglucosamine oligomer and collecting the generated chitinase from the culture, wherein the chitinase-generating bacterium is a marine psychrotrophic bacterium of the genus Vibrio.

The chitinase as a novel enzyme in accordance with the invention can be used for modifying chitin into low molecular substances by allowing the chitinase to react with chitin. Particularly, the inventive chitinase can preferably be used for industrial production of N-acetylglucosamine oligomer.

DESCRIPTION OF THE PREFERRED EMBODIMENTS

The novel chitinase of the invention has an action to cut the β-1,4 bond of chitin in a random manner to generate an oligomer comprising the tetramer and dimer of N-acetylglucosamine as the principal components.

The active temperature range of the inventive novel chitinase characteristically is as wide as 4 to 60° C. More specifically, the inventive chitinase characteristically has unique temperature properties including the property as a psychrotrophic enzyme and additionally the property that the inventive chitinase exerts its activity up to a temperature range higher than those of known chitinase species derived from mesophilic bacteria.

The physico-chemical properties of the inventive chitinase are as follows.

1. Action: random cutting of the β-1,4 bond of chitin to generate the tetramer and dimer of N-acetylglucosamine. Generally, the enzyme decomposes chitin to generate an oligomer comprising the tetramer and dimer of N-acetylglucosamine as the principal components; in case that the action is exerted for a short period of time, multi-mers including 6-mer and more are partially generated. Nevertheless, no N-actylglucosamine monomer is generated.

Figure 1:
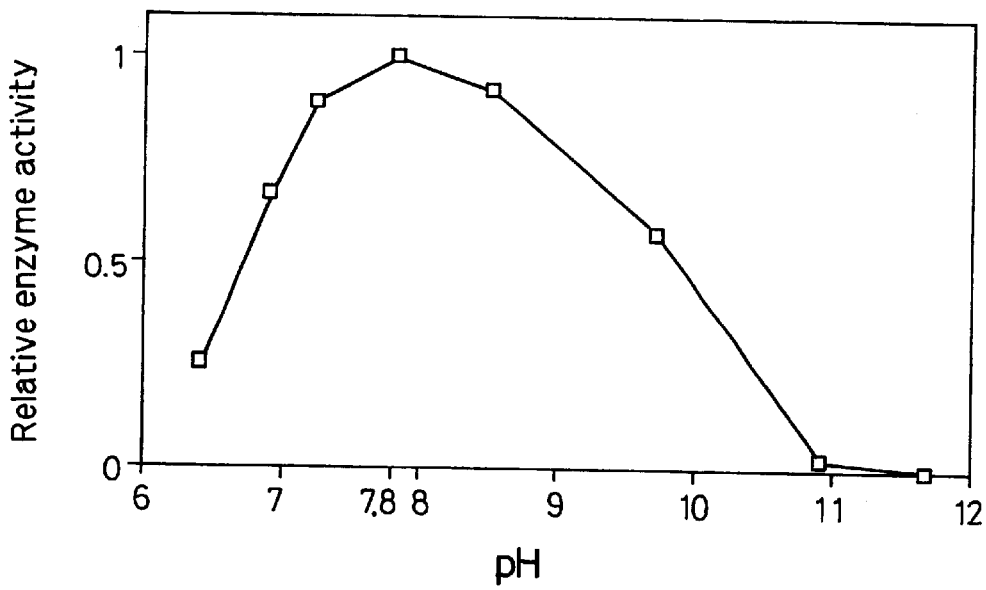
FIG. 1 is an explanatory graph depicting the relation between the relative activity of the inventive chitinase derived from a marine psychrotrophic bacterial strain P2K-5 of the genus Vibrio (FERM BP-5769) on colloidal chitin and pH.

2. Optimum pH: 6.5 to 10.4. The optimum pH is apparently shown in FIG. 1 depicting the graph of the relation between the relative activity of the enzyme (the inventive chitinase) and pH. As shown in FIG. 1, additionally, the peak activity is exerted at pH 7.8. In FIG. 1, the relative activity of the enzyme is particularly high at pH 7.2 to 9.0.

3. Stable pH: 7.0 to 9.0. After heating at pH 7.8 and 30° C. for 30 minutes, for example, 90% of the activity is retained.

4. Optimum temperature: 37° C. The optimum temperature is apparently shown in the graph representing the relation between the relative activity and reaction temperature of the enzyme (the inventive chitinase) in FIG. 2.

Figure 2:
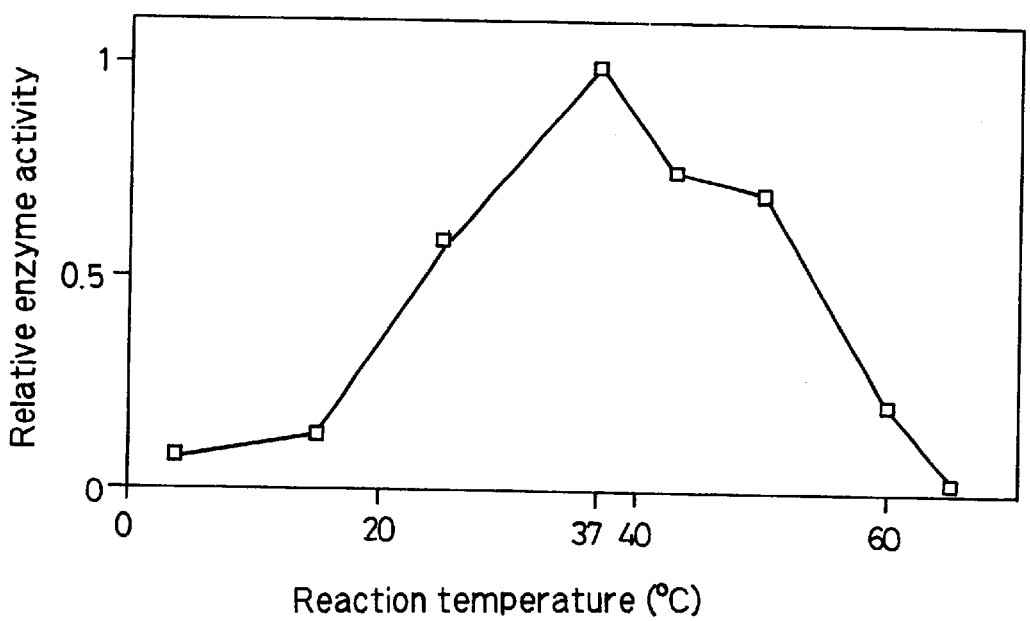
FIG. 2 is an explanatory graph depicting the relation between the relative activity of the chitinase and reaction temperature.

5. Active temperature range: 4 to 60° C. The active temperature range is apparently shown in the graph representing the relation between the relative activity and reaction temperature of the enzyme in FIG. 2. More specifically, the inventive chitinase has a property as a psychrotrophic enzyme and a property such that the activity is exerted up to a higher temperature range than those of conventionally known chitinase derived from mesophilic bacteria. FIG. 2 shows that the relative enzyme activity is particularly high at a reaction temperature of 23 to 50° C.

6. Thermal stability: 60% or more of the initial activity is retained even after heating at 40° C. and pH 8.0 for 30 minutes. As apparently shown in the graph representing the relation between the residual activity and temperature of the enzyme (the inventive chitinase) in FIG. 3, the residual activity after warming or heating at pH 8.0 and below 20° C., at 30° C. and at 40° C. for 30 minutes is 100%, 90% or more and 60% or more, respectively. Additionally, the thermal stability of the enzyme is significantly improved in the co-presence of substrates.

The inventive chitinase sufficiently decomposes chitin in solid, such as powdery chitin in a heterogeneous reaction system. However, the reaction velocity of the inventive chitinase is elevated for substrates such as regenerated chitin such as colloidal chitin and glycol chitin as a water-soluble derivative of chitin.

The enzyme activity of the inventive chitinase was assayed by the following method.

Chitin (manufactured by Katakura Chikkarin, Ltd.) was dissolved in hydrochloric acid, again deposited in water, filtered and rinsed, to prepare colloidal chitin. In a sample tube were placed the colloidal chitin (20 mg) as a substrate, an enzyme solution (1 ml) and 0.4 M phosphate buffer, pH 8.7 (0.2 ml), followed by sealing and agitation at 37° C. for 2 hours. After termination of the reaction, the agitation mixture was centrifuged, to recover the supernatant containing the generated oligomer comprising the tetramer and dimer of N-acetylglucosamine as the principal components; 0.4 ml of the supernatant was transferred in a test tube, where the oligomer was decomposed with commercially available β-N-acetylglucosaminidase to the monomer N-acetylglucosamine. As the β-N-acetylglucosaminidase, satisfactorily, use can be made of a commercially available cellulase "Cellulosin AP" (under trade name; a product manufactured by Ueda Chemical Co.). Cellulosin AP is identical with "Cellulosin AC40" (under trade name; a product manufactured by Hankyu Kyoei Bussan Co., Ltd.). The generated N-acetylglucosamine was subjected to calorimetric assay by the Morgan-Elson method [Kimiko Abe, Nobuko Seno; Seibutu-Kagaku Jikken (Biochemical Experiments), Vol. 11, Sugar Experimental Method, p. 22–23 (1968), Kyoritsu Shuppan].

The quantity of the enzyme (chitinase) generating the oligomer corresponding to 1 μmol N-acetylglucosamine per one minute is defined as one unit of the enzyme.

The novel chitinase of the invention can preferably be produced by culturing a chitinase-generating bacterium reacting with chitin to generate the N-acetylglucosamine oligomer and collecting the chitinase from the culture, wherein the chitinase-generating bacterium is a marine psychrotrophic bacterium of the genus Vibrio.

Any marine psychrotrophic bacterium of the genus Vibrio and with the potency to generate the chitinase can be used as the bacterium according to the method for producing chitinase. For example, the marine psychrotrophic bacterial strain P2K-5 (FERM BP-5769) isolated from the in-depth water in a Boso sea trench in Japan is listed.

The marine psychrotrophic bacterial strain P2K-5 is deposited under the Accession No. FERM BP-5769 at the National Institute of Bioscience and Human-Technology, Agency of Industrial Science and Technology, MITI.

The marine psychrotrophic bacterial strain P2K-5 (FERM BP-5769) generating chitinase is of the following bacteriological properties.

1. Morphological properties
1-1. Cell morphology: rod.
1-2. Flagellum morphology: polar flagellum.
1-3. Gram staining: negative.
2. Physiological Properties
2-1. Growth temperature:
4° C.:+
25° C.:+
30° C.:+
2-2. O-F test: fermentative.
2-3. Salts requirement:+
2-4. Pigment generation:−
2-5. Oxidase:+
2-6. Catalase:+.
3. The source of the Strain Isolated: Sea Water in 6000-m Depth in a Boso sea Trench in Japan.

The aforementioned bacteriological properties were mainly tested according to Yoshio Ezura, Coastal Environment Survey Manual II (Section: Water Quality and Microorganisms), Nippon Marine Academy Association ed., Koseisha Koseikaku, p. 357–364 (1990) and with reference to Kazuo Komagata, Classification and Identification of Microorganisms (No. 2), (revised edition edited by Takeji Hasegawa), Gakkai Shuppan Center, p. 99–161 (1985).

The bacteriological properties based on the Simple Identification Scheme of Marine Bacteria in Marine and Fresh Water [Coastal Environment Survey Manual II (Section: Water Quality and Microorganisms), Nippon Marine Academy Association ed., Koseisha Koseikaku, p. 357–364 (1990)] were compared with the Bergey's Manual of Systematic Bacteriology, Vol. 1 (Noel R. Krieg, John G. Holt ed., Williams & Wilkins, Baltimor, 1984) and the Bergey's Manual of Determinative Bacteriology, the 9-th edition, (John G. Holt, Noel R. Krieg, Peter H. A. Sneath, James T. Staley eds., Williams & Wilkins, Baltimor, 1994). It was identified that the marine psychrotrophic bacterial strain P2K-5 (FERM BP-5769) belonged to the genus Vibrio.

Chitinase production using the marine psychrotrophic bacterial strain P2K-5 (FERM BP-5769) comprises inoculating the bacterium in an appropriate culture medium, preferably in the presence of an induction agent, by a general method. The induction agent includes chitin, regenerated chitin such as colloidal chitin, chitin decomposition products and chitin derivatives such as glycol chitin, singly or in combination with two or more thereof. The induction agent is added at a concentration of generally 0.1 g/liter or more, preferably 1 to 50 g/liter.

Any general culture medium can be used as the culture medium, with no specific limitation. For example, the carbon source includes glucose, maltose, xylose, sucrose and peptone; the nitrogen source includes organic nitrogen such as yeast extract, peptone, meat extract and amino acid solutions and inorganic nitrogen such as ammonium sulfate and ammonium chloride. Additionally, the induction agent can be used satisfactorily as such carbon source and nitrogen source. As the inorganic salt, use can be made of appropriate combinations of magnesium sulfate, magnesium chloride, sodium phosphate, potassium phosphate, potassium chloride, sodium chloride and calcium chloride. The culture medium is adjusted to a range of pH 6.5 to 8.5, with the addition of an appropriate acid or base, which is then sterilized in an autoclave.

The culture conditions are preferably aerobic shaking or agitation culturing at a temperature of 5 to 35° C., preferably 20 to 28° C. for about 20 to 72 hours. The bacterium can be cultured under stationary culture.

The method for separating the bacterium and the culture broth from the resulting culture includes conventional centrifugation method and filtration method, but centrifugation method is preferable. The supernatant per se can be utilized as a crude enzyme solution, but the objective enzyme can be deposited, concentrated and harvested through salting with ammonium sulfate.

For further purifying chitinase from the culture supernatant or from a crude enzyme solution prepared by re-dissolving the precipitate recovered through salting, general enzyme purification means such as salting, ion exchange chromatography, gel filtration, adsorption chromatography, hydrophobic chromatography, preparative electrophoresis are appropriately combined together and used for purification.

In such manner, the novel chitinase of the invention can be recovered.

The invention is now described in more detail in the following examples and test examples.

EXAMPLE 1

The bacterial strain P2K-5 (FERM BP-5769;200 $\mu$l) stored under refrigeration was inoculated in a ½ TZ culture medium (Akihiko Maruyama, Naoki Mita, and Takanori Higashihara, J. oceanogr. 49, 353–376, 1993) (5 ml) in a test tube with "Silico Stopper" (under trade name; Shin-etsu Polymer) and then overnight cultured under shaking at 25° C. The composition of the ½ TZ culture medium was as follows: 2.5 g/liter polypeptone (manufactured by Daigo Co.), 0.5 g/liter yeast extract (manufactured by Difco Co.), 4.77 g/liter HEPES (under trade name; manufactured by Dojin CO.), 21.533 g/liter sodium chloride, 3.607 g/liter sodium sulfate, 0.609 g/liter potassium chloride, 0.176 g/liter sodium hydrogencarbonate, 0.088 g/liter potassium bromide, 0.023 g/liter boric acid, 0.003 g/liter sodium fluoride, 9.747 g/liter magnesium chloride $6H_2O$, 1.368 g/liter calcium chloride. $2H_2O$, and 0.022 g/liter strontium chloride $6H_2O$.

Subsequently, the culture (1 ml) was added to "Marine broth" (under trade name; manufactured by Difco Co.) (100 ml), for further culturing under shaking for 24 hours. The culture (25 ml) was added to a ½ TZ culture medium (1 liter) containing 20 g of chitin powder, for aerobic culturing under shaking at 25° C. for 48 hours. Thereafter, the culture was centrifuged at 8,000×g for 20 minutes; and the resulting supernatant was recovered. The supernatant was adjusted to 80% saturation with solid ammonium sulfate; and the resulting precipitate was collected by centrifugation and dissolved again, to recover a crude enzyme solution at a specific activity of 0.00078 unit/mg · protein and the total activity of 2.30 units.

The crude solution was passed through a column packed with "Butyl Sepharose 4FF" (50 ml) (under trade name; hydrophobic chromatographic resin; manufactured by Pharmacia Co.) preliminarily equilibrated with 0.1 M phosphate buffer, pH 7.0 containing 1.5 M ammonium sulfate, to adsorb the objective enzyme to the resin. After the column was rinsed with the same phosphate buffer and the concentration of ammonium sulfate was modified in a step-wise manner to elute the objective enzyme, an enzyme fraction with the total activity of 1.04 units and a specific activity of 0.0077 unit/mg · protein was recovered.

The active fraction was passed through a column packed with 10 mM "TSKgel Super Q Toyopearl 650 M" (under trade name; ion exchange chromatographic resin; manufactured by Toso Co., Ltd.) preliminarily equilibrated with 10 mM phosphate buffer, pH 7.0, to adsorb the objective enzyme to the resin. After the column was rinsed with the same phosphate buffer and the concentration of NaCl in the phosphate buffer was modified in a step-wise manner to elute the objective enzyme, an enzyme fraction with the total activity of 0.51 unit and a specific activity of 0.078 unit/mg · protein was recovered.

TEST EXAMPLE 1

Using the enzyme (chitinase) fraction with a specific activity of 0.0077 unit/mg · protein as recovered by elution through the column packed with "Butyl Sepharose 4FF" shown in Example 1, the effect of pH on the activity was examined.

A substrate colloidal chitin (20 mg) and the enzyme solution (1 ml; 0.0014 unit) were placed in a sample tube; and the mixture was then adjusted to various pHs by using 0.2 ml of 0.4 M phosphate buffer, for reaction at 30° C. for 2 hours, to recover a supernatant containing the generated oligomer of N-acetylglucosamine through centrifugation. The supernatant of 0.4 ml was transferred in a test tube, followed by addition of 0.1 ml of Cellulosin AP (under trade name; manufactured by Ueda Chemical Co.; aqueous 1% solution), for shaking at 37° C. for 30 minutes; the generated N-acetylglucosamine was subjected to calorimetric assay by the Morgan-Elson method.

The relation between the relative activity of the resulting chitinase and pH is shown in FIG. 1.

TEST EXAMPLE 2

Using the enzyme (chitinase) fraction with a specific activity of 0.0077 unit/mg · protein as recovered by elution through the column packed with "Butyl Sepharose 4FF" shown in Example 1, the relation between chitinase activity and reaction temperature was examined as follows.

A substrate colloidal chitin (20 mg) and the enzyme solution (1 ml; specific activity of 0.0014 unit) were placed in a sample tube; and the mixture was then adjusted to pH 7.8 by using 0.2 ml of 0.4 M phosphate buffer, for reaction at various temperatures for 2 hours, to recover a supernatant containing the generated oligomer of N-acetylglucosamine through centrifugation. The supernatant of 0.4 ml was transferred in a test tube, followed by addition of 0.1 ml of Cellulosin AP (under trade name; manufactured by Ueda Chemical Co.; aqueous 1% solution), for shaking at 37° C. for 30 minutes; the generated N-acetylglucosamine was subjected to calorimetric assay by the Morgan-Elson method.

The relation between the relative activity of the resulting chitinase and reaction temperature is shown in FIG. 2.

TEST EXAMPLE 3

Using the enzyme (chitinase) fraction with a specific activity of 0.0077 unit/mg·protein as recovered by elution through the column packed with "Butyl Sepharose 4FF" shown in Example 1, the thermal stability of chitinase was examined.

An enzyme solution (1 ml; 0.0014 unit) was placed in a sample tube, adjusted to pH 8.0 using 0.2 ml of 0.4 M phosphate buffer and left to stand at various temperatures for 30 minutes; then, a substrate colloidal chitin (20 mg) was added, for shaking at 30° C. for 2 hours. Subsequently, a supernatant containing the generated oligomer of N-acetylglucosamine was recovered through centrifugation. The supernatant of 0.4 ml was transferred in a test tube, followed by addition of 0.1 ml of Cellulosin AP (under trade name; manufactured by Ueda Chemical Co.; aqueous 1% solution), for shaking at 37° C. for 30 minutes; the generated N-acetylglucosamine was subjected to colorimetric assay by the Morgan-Elson method.

Figure 3:
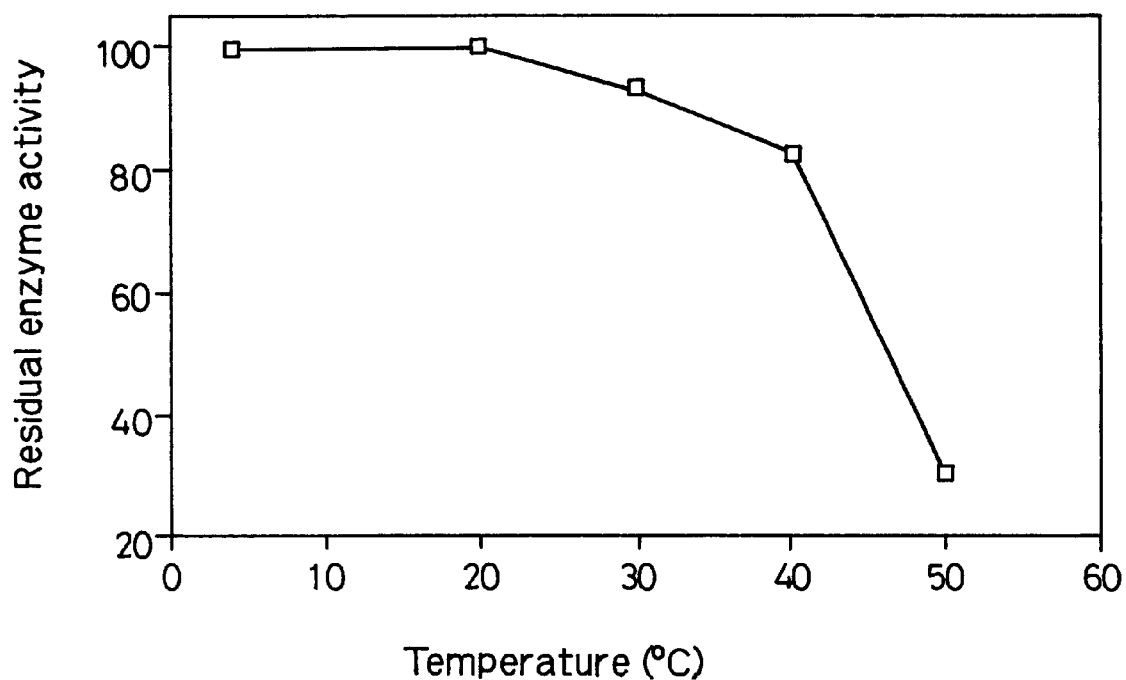
FIG. 3 is an explanatory graph depicting the relation between the residual activity of the chitinase and temperature.

The residual activity at various temperatures is shown in FIG. 3, compared with the enzyme activity in a sample tube preliminarily containing the enzyme solution and colloidal chitin, for reaction at 30° C. for 2 hours.

In accordance with the invention, significantly advantageously, the novel chitinase can be provided, having useful functions such as the production of the oligomer comprising the tetramer and dimer of N-acetylglucosamine by decomposing chitin and having high activity at low temperature as well as even at high temperature, namely a wide active temperature range, so the chitinase can be used under a wide variety of conditions. In accordance with the invention, the other advantage is brought about, furthermore, namely the method for producing the chitinase, which can efficiently be applied industrially.

A technique for producing the oligomer at high purity and with useful physiological activities such as antibacterial activity, anti-viral activity, anti-tumor activity and immuno-potentiation in a simple manner, with no use of chemical products such as alkalis or acids demanding enormous disposal cost and labor, can be provided.

What is claimed is:

1. Chitinase with the following physico-chemical properties 1 to 6:
   1. action: random cutting of the β-1,4 bond of chitin to generate the tetramer and dimer of N-acetylglucosamine;
   2. optimum pH: 6.5 to 10.4;
   3. stable pH: 7.0 to 9.0;
   4. optimum temperature: 37° C.;
   5. active temperature range: 4 to 60° C.; and
   6. thermal stability: 60% or more of the initial activity is retained even after heating at 40° C. and pH 8.0 for 30 minutes.

2. A method for producing chitinase, comprising:

culturing a chitinase-generating bacterium of a marine psychrotrophic bacterial strain P2K-5 of the genus Vibrio (FERM BP-5769), and collecting the generated chitinase from the culture, wherein the chitinase reacts with chitin to generate N-acetylglucosamine oligomer and has the following physico-chemical properties:

action: random cutting of the β-1,4 bond of chitin to generate tetramer and dimmer of N-acetylglucosamine;

optimum pH: 6.5 to 10.4;

stable pH: 7.0 to 9.0;

optimum temperature: 37° C.;

active temperature range: 4 to 60° C., and thermal stability: 60% or more of the initial activity is retained even after heating at 40° C. and pH 8.0 for 30 minutes.

* * * * *